United States Patent [19]

van Andel

[11] Patent Number: Plant 5,499

[45] Date of Patent: Jun. 25, 1985

[54] CARNATION NAMED STANBLANCA

[75] Inventor: Jacob van Andel, Aalsmeer, Netherlands

[73] Assignee: B. V. Handelskwekerij, M. C. van Staaveren, Aalsmeer, Netherlands

[21] Appl. No.: 556,612

[22] Filed: Nov. 30, 1983

[51] Int. Cl.[3] ..... A01H 5/00

[52] U.S. Cl. ..... Plt./70

[58] Field of Search ..... Plt./70

*Primary Examiner*—Robert E. Bagwill

*Attorney, Agent, or Firm*—Charles W. Rummler

[57] ABSTRACT

A new variety of carnation plant having pale yellow blooms of medium size with a relatively large number of petals, the flowers being produced continuously and profusely on upright flower stems of good strength, the plant itself having a vigorous, upright growth habit with abundant production of foliage and characterized by its flowers being less susceptible to fusarium oxysporum.

1 Drawing Figure

BACKGROUND OF THE NEW PLANT

My new carnation variety was discovered by me in 1977 as a sport of the variety "Londorga" being grown for commercial purposes in greenhouse at Aalsmeer, The Netherlands, and this particular plant was selected for propagation and test because of its lovely pale yellow flowers of medium size and of excellent appearance because of the relatively large number of petals comprising each bloom. Propagation of this discovery plant was done by me by means of cuttings at Aalsmeer with very good results, which prompted me to carry on propagation in the same manner through several successive generations and over a period of several years, by which I found that the novel and distinctive characteristics of this new variety were fully retained from generation to generation and appeared to be firmly fixed.

DESCRIPTION OF THE DRAWING

My new variety of carnation plant is illustrated by the accompanying photographic drawing which shows, in full color, a three-quarter view of a mature bloom and partial face views of companion blooms, the entire drawing being intended to illustrate the nature of the blooms of this new plant. The color shown is as nearly true to that of the natural flower as herein specified as it is reasonably possible to obtain by conventional commercial photographic procedures.

DESCRIPTION OF THE NEW PLANT

The following is a detailed description of my new carnation plant based upon observations of greenhouse grown plants made at Aalsmeer, The Netherlands, in the summer of 1983, the color designations being according to The R.H.S. Colour Chart published by The Royal Horticultural Society of London, England.

THE PLANT

Origin: Sport.
Parentage: Carnation "Londorga" (unpatented).
Classification:
- *Botanic.*—Hybrid *Dianthus caryophyllus.*
- *Commercial.*—Greenhouse carnation.

Form: Bush.
Height: Normal.

Growth: Upright and with good strength and normal branching.
Foliage:
- *Quantity.*—Abundant.
- *Number of leaves.*—Varying according to season.
- *Size of leaf.*—Medium.
- *Shape.*—Oblong.
- *Texture.*—Smooth.
- *Color.*—Both upper and under sides — Blue Green with waxy layer.

THE BUD

Size: Medium.
- *Diameter.*—About 15 mm.
- *Length.*—About 30 mm.

Shape: Generally cylindrical.
Sepals: Normal and curl back when flowers open.
- *Color.*—Inside and outside — Grey/Green.

Calyx:
- *Shape.*—Funnel-shaped.
- *Size.*—Medium.
- *Aspect.*—Smooth.
- *Splitting.*—The calyx rarely splits.

THE FLOWER

Blooming habit: Continuous.
Size of bloom: Medium.
- *Diameter.*—About 80 mm.
- *Depth.*—About 40 mm.

Shape: High centered when bloom first opens and as bloom matures.
Petalage:
- *Number of petals.*—From 50 to 60.
- *Arrangement.*—Loosely imbricated.
- *Form.*—Fan-shaped with generally serrated to dentate margins.
- *Texture.*—Soft.
- *Appearance.*—Shiny.
- *Color.*—All petals: Top side — Body — R.H.S. 4D. Base — Pale Green. Reverse side — R.H.S. 4D. The color is the same for all seasons.

Flower stem:
- *Length.*—Varies in the course of the season.
- *Character.*—Strong and upright.
- *Color.*—Dark Green.

Persistence: The petals hang on and dry.
Fragrance: Slight.

Disease resistance: Less susceptible to fusarium oxysporum as observed in the area of Aalsmeer, The Netherlands.

Lasting quality:

*On plant.*—About 15 days.

*As a cut flower.*—From 8 to about 12 days.

REPRODUCTIVE ORGANS

Stamens: Average in number and arrangement.

*Anthers.*—Size: Medium. Color: Cream.

*Pollen.*—Color — Cream (if present).

Pistils:

*Number.*—One.

*Style.*—Length: About 30 mm.

This new plant most nearly resembles its parent variety "Londorga" in most of its characteristics except its novel color and its resistance to fusarium oxysporum.

I claim:

1. The new and distinct variety of carnation plant, substantially as herein shown and described, characterized by its continuous production of light yellow flowers of medium size and large quantity of loosely imbricated petals.

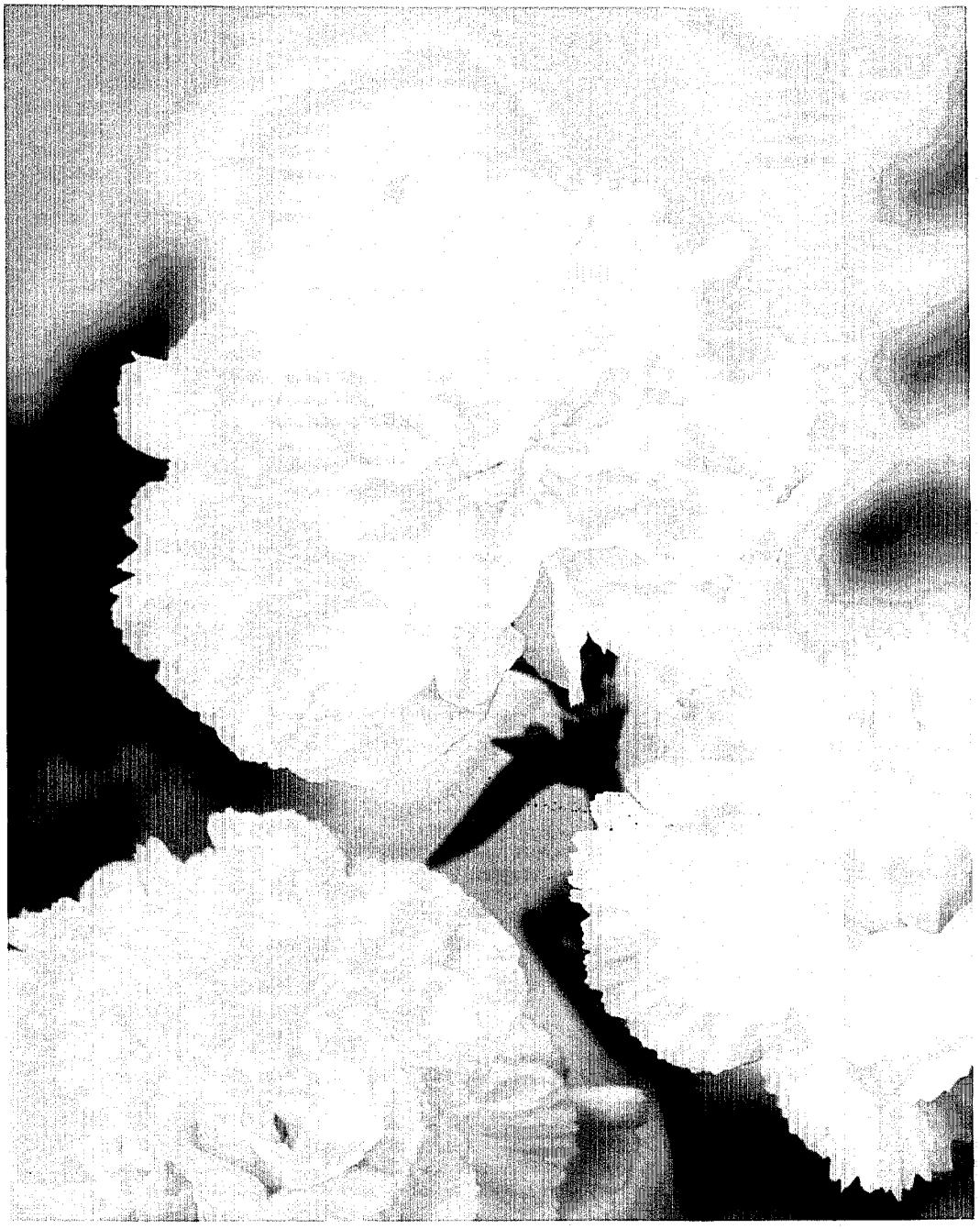

* * * * *